United States Patent [19]

Soula et al.

[11] 4,346,244

[45] Aug. 24, 1982

[54] PREPARATION OF CHLOROALKOXYBENZENES

[75] Inventors: Gérard Soula, Meyzieu; Louis Linguenheld, Ruelisheim, both of France

[73] Assignee: Rhone-Poulenc Industries, Paris, France

[21] Appl. No.: 242,540

[22] Filed: Mar. 11, 1981

[30] Foreign Application Priority Data

Mar. 12, 1980 [FR] France ................................ 80 05489

[51] Int. Cl.$^3$ .............................................. C07C 41/16
[52] U.S. Cl. ................................... 568/656; 568/588; 568/642; 568/647
[58] Field of Search ................. 568/656, 647, 588, 642

[56] References Cited

U.S. PATENT DOCUMENTS

| | | | |
|---|---|---|---|
| 2,803,664 | 8/1957 | Redman | 568/656 |
| 2,949,488 | 8/1960 | Rocklin | 568/656 X |
| 3,055,950 | 9/1962 | Fike et al. | 568/656 X |
| 4,057,585 | 11/1977 | Mendelson | 568/656 |
| 4,287,125 | 9/1981 | Soula | 568/647 X |

*Primary Examiner*—Bernard Helfin
*Attorney, Agent, or Firm*—Burns, Doane, Swecker & Mathis

[57] ABSTRACT

Chloroalkoxybenzenes are prepared by reacting a polychlorobenzene with at least one alkali metal hydroxide and an alcohol, ROH, in the presence of at least one tertiary amine sequestering agent having the formula:

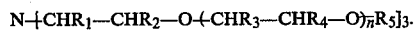

N$\pm$CHR$_1$—CHR$_2$—O$\pm$CHR$_3$—CHR$_4$—O$)_n$R$_5$]$_3$.

20 Claims, No Drawings

PREPARATION OF CHLOROALKOXYBENZENES

BACKGROUND OF THE INVENTION

1. Field of the Invention

The present invention relates to the preparation of chloroalkoxybenzenes, and, more especially, to the preparation of chloroalkoxybenzenes from chlorobenzene starting materials.

2. Description of the Prior Art

It is known to this art to prepare chloroalkoxybenzenes from chlorobenzene precursors. Thus, the preparation of 2,3-dichloroanisole by reaction of sodium methylate with 1,2,3-trichlorobenzene in methanol, at a temperature of 180° C. and under pressure, has been described [*Recueil des Travaux Chimiques des Pays-Bas* (Reports of Chemical Work in the Netherlands), 37, 200]. Such process, however, is not applicable on an industrial scale, because numerous by-products result therefrom and the yields obtained are very low.

And in U.S. Pat. No. 4,057,585 there is described the preparation of 2,3-dichloro-1-alkoxybenzene by reacting an alkali metal lower alkoxide with 1,2,3-trichlorobenzene, at 100°–200° C., in an inert solvent selected from the group consisting of dimethylformamide, dimethylacetamide and dimethylsulfoxide, the reaction taking place in the presence of methanol or ethanol in amounts sufficient to solvate the alkali metal alkoxide. In this particular type of process, two major disadvantages militate against the industrial application thereof. The first is predicated upon the fact that it is necessary to employ a completely anhydrous alkali metal alkoxide, thus prepared from the corresponding alkali metal in metallic form. Indeed, an alkoxide devoid of sodium hydroxide must be utilized, lest the NaOH degrade the solvent medium. The second disadvantage resides in the fact that the required solvents are on the one hand, burdensome, and on the other are but poorly adapted for use on an industrial scale, by reason of the necessity for the distillation and recycling thereof.

Further, in Sam and Simmons, *Journal of the American Chemical Society*, 96, No. 17, p. 2252 (1974), there is disclosed the reaction of o- or m-dichlorobenzene with potassium methylate complexed with an equimolecular amount of a crown ether (18-dicyclohexyl-6-crown). This technique is not especially worthwhile, though, both by reason of the economy of the process, and, secondly, because of the complexity thereof. Indeed, "crown ethers" are quite costly compounds. Furthermore, it too is necessary to prepare the crown ether-alcoholate complex in a separate step.

SUMMARY OF THE INVENTION

Accordingly, a major object of the present invention is the provision of an improved process for the preparation of the chloroalkoxybenzenes, which process is devoid of those disadvantages and drawbacks to date characterizing the state of this art, and which features reacting a polychlorobenzene having the structural formula (I):

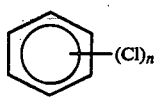

wherein n ranges from 2 to 6 ($2 \leq n \leq 6$), with at least one alkali metal hydroxide and an alkanol having the formula ROH (II), wherein R contains from 1 to about 12 carbon atoms, in the presence of a sequestering agent having the structural formula (III):

$$N \text{---} [CHR_1 \text{---} CHR_2 \text{---} O \text{---} (CHR_3 \text{---} CHR_4 \text{---} O)_{\overline{n}} R_5]_3 \quad (III)$$

wherein n is a number greater than or equal to 0 and less than or equal to about 10 ($0 \leq n \leq 10$), $R_1$, $R_2$, $R_3$, $R_4$, which may be identical or different, each represents a hydrogen atom or an alkyl radical having from 1 to 4 carbon atoms and $R_5$ represents an alkyl or cycloalkyl radical having from 1 to 12 carbon atoms, a phenyl radical or a radical of the formula —$C_mH_{2m}$—$\phi$, or $C_mH_{2m+1}$—$\phi$—, with m ranging from 1 to about 12 and $\phi$ being phenyl.

DETAILED DESCRIPTION OF THE INVENTION

More especially according to this invention, and while applicants do not wish to be bound by any particular theory, it would appear that the sequestering agent of Formula (III) forms, with the alkali metal alcoholate resulting from the reaction of ROH with the alkali metal hydroxide, a complex which is soluble in the benzene derivative having the Formula I. The reaction, therefore, may be conducted in the absence of solvent.

According to a preferred embodiment of the invention, a mixture of the alkali metal hydroxide or hydroxides with the ROH alcohol is introduced into a mixture of polychlorobenzene containing the sequestering agent or agents, with the alkali metal alcoholate required for the reaction thus being generated in situ. One of the principal advantages of the process according to the invention, as is readily apparent, is that it is not necessary, as with the prior art, to employ either an alkali metal in metallic form or to preliminarily isolate the sequestering agent/alkali metal alcoholate complex.

According to a preferred embodiment of the invention a sequestering agent of the formula (I) is used in which $R_1$, $R_2$, $R_3$ and $R_4$ represent a hydrogen atom or a methyl radical, $R_5$ and n being as above-defined.

Among such sequestering agents, it is even more particularly preferred to use those in which n is greater than or equal to 0 and less than or equal to 6 and in which $R_5$ represents an alkyl radical having from 1 to 4 carbon atoms.

The following sequestering agents are noted as illustrative:

[1] tris-(3-oxabutyl)-amine of the formula:

N—(CH$_2$—CH$_2$—O—CH$_3$)$_3$

[2] tris-(3-oxaheptyl)-amine of the formula:

N—(CH$_2$—CH$_2$—O—C$_4$H$_9$)$_3$

[3] tris-(3,6-dioxaheptyl)-amine of the formula:

N—(CH$_2$—CH$_2$—O—CH$_2$—CH$_2$—O—CH$_3$)$_3$

[4] tris-(3,6,9-trioxadecyl)-amine of the formula:

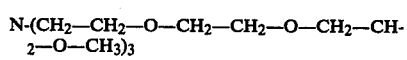

N-(CH$_2$—CH$_2$—O—CH$_2$—CH$_2$—O—CH$_2$—CH$_2$—O—CH$_3$)$_3$

[5] tris-(3,6-dioxaoctyl)-amine of the formula:

N—(CH$_2$—CH$_2$—O—CH$_2$—CH$_2$—O—C$_2$H$_5$)$_3$

[6] tris-(3,6,9-trioxaundecyl)-amine of the formula:

N—(CH₂—CH₂—O—CH₂—CH₂—O—CH₂—CH₂—O—C₂H₅)₃

[7] tris-(3,6-dioxanonyl)-amine of the formula:

N—(CH₂—CH₂—O—CH₂—CH₂—O—C₃H₇)₃

[8] tris-(3,6,9-trioxadodecyl)-amine of the formula:
N—(CH₂—CH₂—O—CH₂—CH₂—O—CH₂—CH₂—O—C₃H₇)₃

[9] tris-(3,6-dioxadecyl)-amine of the formula:

N—(CH₂—CH₂—O—CH₂—CH₂—O—C₄H₉)₃

[10] tris-(3,6,9-trioxatridecyl)-amine of the formula:

N—(CH₂—CH₂—O—CH₂—CH₂—O—CH₂—CH₂—O—C₄H₉)₃

[11] tris-(3,6,9,12-tetraoxatridecyl)-amine of the formula:

N—(CH₂—CH₂—O—(CH₂—CH₂—O)₃—CH₃)₃ and
[12] tris-(3,6,9,12,15,18-hexaoxanonadecyl)-amine of the formula:

N—(CH₂—CH₂—O—(CH₂—CH₂—O)₅—CH₃)₃

The following sequestering agents are also representative:
[13] tris-(3,6-dioxa-4-methylheptyl)-amine of the formula:

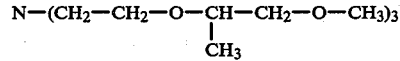

and
[14] tris-(3,6-dioxa-2,4-dimethylheptyl)-amine of the formula:

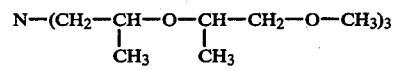

The amine sequestering agents utilized in the process according to the invention are per se known to the prior art. Thus, French Pat. No. 1,302,365 describes the preparation of the tertiary amines N—(CH₂—CH₂—O—CH₃)₃ and N—(CH₂—CH₂—O—CH₂—CH₂—O—CH₃)₃ as by-products from the synthesis of the corresponding primary and secondary amines, such primary and secondary amines being valuable as intermediates in the synthesis of various pharmaceuticals, as corrosion inhibitors, as intermediates in the synthesis of agricultural chemicals, and as emulsifiers. It will also be appreciated, though, that the prior art, including the aforenoted French Pat. No. 1,302,365, is conspicuously devoid of any suggestion that the topic amines could be utilized in any reaction within the ambit of this invention.

The alkali metal hydroxide is preferably either sodium hydroxide or potassium hydroxide.

It is especially preferred to utilize potassium hydroxide, or a mixture of potassium hydroxide and sodium hydroxide. In the latter case, a mixture containing at least 50% potassium hydroxide is most preferred.

The amount used of the sequestering agent having the Formula (III) is preferably such that the molar ratio of the sequestering agent to the alkali metal hydroxide ranges from about 0.001 to about 0.2. This ratio more preferably ranges from about 0.01 to about 0.1.

Representative of the starting materials having the structural Formula (I), exemplary are: para-dichlorobenzene, ortho-dichlorobenzene, meta-dichlorobenzene, 1,2,4-trichlorobenzene, 1,2,3-trichlorobenzene, 1,3,5-trichlorobenzene, tetrachlorobenzene, pentachlorobenzene and hexachlorobenzene.

It too is within the ambit of this invention to utilize polychlorobenzenes containing 2 to 5 chlorine atoms and further comprising at least one additional inert substituent that does not react chemically in any reaction consistent herewith.

As examples of non-limiting inert substituents of the aforesaid type, the following are illustrative: alkyl, phenyl, NO₂ radicals. The latter may be of interest in certain instances, to the degree that same activate the benzene ring.

Exemplary of the alcohols having the Formula (II) and especially preferred in the subject process are: methanol, ethanol, isopropanol, the butanols, cyclohexanol, octanol, and the like.

And representative of the final product chloroalkoxybenzenes that may be prepared according to the process of this invention, the following compounds are exemplary: ortho-, meta- or para-chloroanisole, 2,3-dichloroanisole, 2,6-dichloroanisole, 2,5-dichloroanisole, 2,4,5-trichloroanisole, 2,3,6-trichloroanisole, 2,3,4,6-tetrachloroanisole, pentachloroanisole, 2,3-dichloroethoxybenzene, 2,5-dichloroethoxybenzene, and 2,5-dichloroisopropoxybenzene.

It is preferred to utilize the compounds of the Formula (I) and the alkali metal hydroxide in amounts such that the molar ratio of the alkali metal hydroxide to the compound (I) ranges from between about 0.5 to about 3. Even more preferred is a ratio ranging from between about 0.8 to about 2.5.

The amount used of the alcohol (II) may also vary between wide limits. Preferably, an amount of alcohol (II) is used such that the molar ratio of ROH to the alkali metal hydroxide ranges from 1 to 15. Even more preferred is a ratio ranging from 6 to 8.

The subject reaction is advantageously conducted at a temperature ranging from about 80° C. to about 250° C., and preferably at a temperature ranging from 100° C. to 180° C.

The reaction is also typically conducted at atmospheric pressure, albeit pressures either higher or lower than atmospheric too are envisaged.

And while not strictly necessary, a third solvent may even be used, such as, for example, toluene, o-, p- or m-xylene, or chlorobenzene.

The sequestering agents used in the process according to the invention can be conveniently prepared in the following manner:

These compounds can be prepared by condensing a salt of the formula:

in which $R_3$, $R_4$, $R_5$ and n are as above-defined and in which M represents an alkali metal atom selected from among sodium, potassium and lithium, either with an amine having the structural formula:

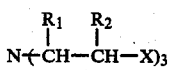

in which $R_1$ and $R_2$ are as defined above and X represents chlorine or bromine, or with the corresponding hydrochloride or hydrobromide.

The molar ratio alkali metal salt/amine desirably is between about 3 and about 5.

The condensation is carried out at a temperature between 100° and 150° C. for 1 to 15 hours, in the presence of a solvent which can be, for example, chlorobenzene or, preferably, the ethylene glycol monoalkyl ether having the formula:

The reaction is preferably carried out in such manner that the solution contains from 2 to 5 moles of alkali metal salt per liter of solvent.

The mixture upon completion of the reaction essentially consists of the tertiary amine of the formula:

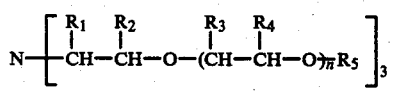

but also contains a small proportion of the corresponding secondary amine:

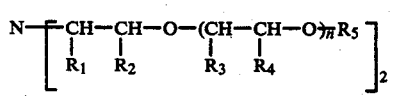

and traces of the primary amine:

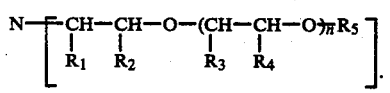

The tertiary, secondary and primary amines are typically present in the ratio 90:8:2, respectively, after distillation.

The aforesaid mixture obtained after a first distillation, i.e., the mixture containing the three different types of amines, can be used directly in the process according to the invention.

For better results consistent with the invention, a more thorough distillation of the above mixture is preferably carried out in order to obtain an essentially pure tertiary amine.

In order to further illustrate the present invention and the advantages thereof, the following specific examples are given, it being understood that same are intended only as illustrative and in nowise limitative.

EXAMPLE 1

Preparation of 2,3-dichloroanisole from trichlorobenzene

Into a three-necked, round-bottomed flask equipped with an agitator, a thermometer, a dropping funnel and a distillation column, the following ingredients were introduced:
(i) 1815 g [10 moles] of 1,2,3-trichlorobenzene, and
(ii) 162 g [0.5 mole] of tris(3,6-dioxaheptyl)amine.

The resulting reaction mass was heated to a temperature of 140° C. and there was next commenced continuous addition thereto, by pouring, of a previously prepared solution of potassium hydroxide in methanol, said solution having been prepared from:
(iii) 1302.5 g [20 moles] of potassium hydroxide tablets, 86%, and
(iv) 2500 g [78.1 moles] of methanol.

The pouring and the heating were controlled such as to maintain a temperature of 135° C. in the reaction mass while the methanol was distilled. The pouring of the potassium hydroxide was for a duration of 1 hour and 15 minutes, and then the reaction mass was maintained at a temperature of 135° C. for 1 hour and 15 minutes for completion of the reaction.

After cooling, 2800 g water were added to extract the salts. The organic layer was decanted and the aqueous layer extracted with 1000 g dichloromethane. After drying, the organic layer was distilled to obtain:
(1) 100 g [0.55 mole] of 1,2,3-trichlorobenzene,
(2) 454 g [2.565 moles] of 2,6-dichloroanisole, and
(3) 700 g [3.955 moles] of 2,3-dichloroanisole.

The rate of transformation of the trichlorobenzene was thus 93.15% and the yield in respect of 2,3-dichloroanisole was 39.5%.

By acidifying the aqueous layer, 342 g of dichlorophenols were recovered, principally 2,6-dichlorophenol.

EXAMPLE 2

The following ingredients were charged into the apparatus described in Example 1:
(i) 363 g [2 moles] of 1,2,3-trichlorobenzene,
(ii) 32 g [0.1 mole] of tris(3,6-dioxaheptyl)amine.

The reaction mixture was heated to 130° C. and a methanol solution of sodium hydroxide and potassium hydroxide, previously prepared by dissolving 117.2 g [1.8 moles] of potassium hydroxide, 86%, and 74.2 g [1.8 moles] of sodium hydroxide, 97%, in 800 g methanol, was continuously poured therein over a period of 1 hour and 30 minutes.

The methanol was distilled off at the rate the solution was poured.

Upon completion of such addition of solution, the reaction mass was maintained at a temperature of 130°-140° C. for a period of 3 hours, 30 minutes.

After cooling, the reaction mass was treated as in Example 1.

The rate of transformation was 84.5% and the yield in respect of 2,3-dichloroanisole was 39% and in 2,6-dichloroanisole of 37%.

EXAMPLE 3

Into the apparatus described in Example 1 and employing the same operating technique, the following ingredients were introduced:
(i) 363 g [2 moles] of 1,2,3-trichlorobenzene, (ii) 42 g [0.09 mole] of tris(3,6,9-trioxadecyl)amine, and (iii) a methanolic solution of potassium hydroxide previously prepared by dissolving 234.4 g [3.6 moles] of potassium hydroxide, 86%, in 400 g of methanol.

After 3 hours at a temperature of 125° C., the reaction mass was treated as in the preceding examples.

The rate of transformation was 94.8% and the yield in respect of 2,3-dichloroanisole was 42% and in respect of 2,6-dichloroanisole was 37%.

EXAMPLE 4

Into the apparatus described in Example 1 and employing the same operating technique, the following ingredients were introduced:

(i) 363 g [2 moles] of 1,2,3-trichlorobenzene, (ii) 32 g [0.1 mole] of tris(3,6-dioxaheptyl)amine, and (iii) a methanolic solution of sodium hydroxide and potassium hydroxide previously prepared by dissolving 156.3 g [2.4 moles] of potassium hydroxide, 86%, and 49.5 g [1.2 moles] of sodium hydroxide, 97%, in 610 g methanol.

After 4 hours at a temperature of 125° C., the reaction mass was treated as in Example 1.

The rate of transformation was 94.1% and the yield in respect of 2,3-dichloroanisole was 38% and in respect of 2,6-dichloroanisole was 35%.

EXAMPLE 5

Into the apparatus described in Example 1 and employing the same operating technique, the following ingredients were introduced:

(i) 363 g [2 moles] of 1,2,3-trichlorobenzene, and (ii) 32 g [0.1 mole] of tris(3,6-dioxaheptyl)amine.

This reaction mixture was heated to a temperature of 140° C. and a butanol solution of KOH, previously prepared by dissolving 248 g [3.80 moles] of potassium hydroxide, 86%, in 741 g [10 moles] normal butanol, was continuously poured therein.

After such addition was completed, the reaction mass was agitated for 5 hours at 140°–145° C.

After treatment per Example 1, the following compounds were recovered by distillation:

(1) 221 g [1.01 mole] of 2,6-dichlorobutoxybenzene, $Bp_{16}$: 140°; and (2) 133.7 g [0.615 mole] of 2,3-dichlorobutoxybenzene, $Bp_{16}$: 147°.

The rate of transformation was 94.5% and the yields were respectively 63.4% in respect of the 2,6-dichlorobutoxybenzene isomer and 32.3% in respect of the 2,3-dichlorobutoxybenzene isomer.

EXAMPLE 6

Preparation of 2,3-dichloroanisole from 1,2,3-trichlorobenzene

Into a three-necked, round-bottomed 2 liter flask, equipped with an agitator, a thermometer and a distillation column, the following ingredients were introduced:

(i) 544.5 g [3 moles] of 1,2,3-trichlorobenzene, (ii) 856 g [26.75 moles] of methanol, (iii) 48 g [0.148 mole] of tris(3,6-dioxaheptyl)amine, and (iv) 195 g [3 moles] of potassium hydroxide, 86%.

This reaction mixture was brought to boiling temperatures and methanol was recovered until a temperature of 140°–150° C. was attained in the mass. The reaction mass was then a semi-crystalline paste and the reaction had taken 2 hours, 30 minutes.

After cooling, 900 g of water were added to dissolve the salts and the organic layer was decanted. The aqueous layer was extracted with 200 g methylene chloride.

The organic layers were combined and distilled to obtain:

(1) 200 g [1.1 moles] of unreacted trichlorobenzene, (2) 131 g [0.74 mole] of 2,6-dichloroanisole, and (3) 142 g [0.80 mole] of 2,3-dichloroanisole.

The tris(3,6-dioxaheptyl)amine was determined to be intact in the distilland.

In this experiment, the rate of transformation was 63% and the yield in respect of 2,3-dichloroanisole was 42.5%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a chloroalkoxybenzene, comprising reacting a polychlorobenzene having the structural formula (I):

wherein n ranges from 2 to 6, with at least one alkali metal hydroxide and alcohol having the formula ROH (II), wherein R contains from 1 to about 12 carbon atoms, in the presence of an effective amount of at least one tertiary amine sequestering agent having the formula (III):

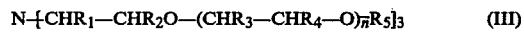

wherein n is a number greater than or equal to 0 and less than or equal to about 10, $R_1$, $R_2$, $R_3$, $R_4$, which may be identical or different, each represents a hydrogen atom or an alkyl radical having from 1 to 4 carbon atoms and $R_5$ represents an alkyl or cycloalkyl radical having from 1 to 12 carbon atoms, a phenyl radical or a radical of the formula $-C_mH_{2m}-\phi$, or $C_mH_{2m+1}-\phi-$, with m ranging from 1 to about 12 and $\phi$ being phenyl.

2. The process as defined by claim 1, wherein the formula (III), $R_1$, $R_2$, $R_3$ and $R_4$ are each hydrogen or methyl.

3. The process as defined by claims 1 or 2, wherein the formula (III), n is an integer which is greater than or equal to 0 and less than or equal to 6.

4. The process as defined by claims 1 or 2, wherein the formula (I), $R_5$ is an alkyl radical having from 1 to 4 carbon atoms.

5. The process as defined by claims 1 or 2, wherein the formula (III), $R_1$, $R_2$, $R_3$ and $R_4$, which are identical or different, are each hydrogen or methyl, n is an integer which is greater than or equal to 0 and less than or equal to 6 and $R_5$ is an alkyl radical having from 1 to 4 carbon atoms.

6. The process as defined by claim 5, wherein the tertiary amine of the formula (III) is tris-(3,6-dioxaheptyl)-amine of the formula:

$$N-(CH_2-CH_2-O-CH_2-CH_2-O-CH_3)_3.$$

7. The process as defined by claim 5, wherein the tertiary amine of the formula (III) is tris-(3,6,9-trioxadecyl)-amine of the formula:

$$N-(CH_2-CH_2-O-CH_2-CH_2-O-CH_2-CH_2-O-CH_3)_3.$$

8. The process as defined by claim 1, wherein the tertiary amine of the formula (III) is selected from the group consisting of tris-(3-oxabutyl)-amine, tris-(3-oxaheptyl)-amine, tris-(3,6-dioxaheptyl)-amine, tris-(3,6,9-trioxadecyl)-amine, tris-(3,6-dioxaoctyl)-amine, tris-(3,6,9-trioxaundecyl)-amine, tris-(3,6-dioxanonyl)-amine, tris-(3,6,9-trioxadodecyl)-amine, tris-(3,6-dioxadecyl)-amine, tris-(3,6,9-trioxatridecyl)-amine, tris-(3,6,9,12-tetraoxatridecyl)-amine, tris-(3,6,9,12,15,18-hexaoxanonadecyl)-amine, tris-(3,6-dioxa-4-methylheptyl)-amine, and tris-(3,6-dioxa-2,4-dimethylheptyl)-amine.

9. The process as defined by claim 1, wherein the alcohol ROH is methanol, ethanol, isopropanol, a butanol, cyclohexanol or octanol.

10. The process as defined by claims 1 or 9, wherein the polychlorobenzene (I) is para-dichlorobenzene, orthodichlorobenzene, meta-dichlorobenzene, 1,2,4-trichlorobenzene, 1,2,3-trichlorobenzene, 1,3,5-trichlorobenzene, tetrachlorobenzene, pentachlorobenzene or hexachlorobenzene.

11. The process as defined by claim 10, wherein the at least one alkali metal hydroxide is sodium hydroxide and/or potassium hydroxide.

12. The process as defined by claim 11, wherein the at least one alkali metal hydroxide is a mixture of sodium hydroxide and potassium hydroxide, said mixture comprising at least 50% potassium hydroxide.

13. The process as defined by claim 10, wherein the molar ratio of alkali metal hydroxide to polychlorobenzene (I) ranges from about 0.5 to about 3.

14. The process as defined by claim 13, said molar ratio ranging from about 0.8 to about 2.5.

15. The process as defined by claim 13, wherein the molar ratio of alcohol (II) to the alkali metal hydroxide ranges from about 1 to about 15.

16. The process as defined by claim 15, said molar ratio ranging from about 6 to about 8.

17. The process as defined by claim 15, said reaction being conducted at a temperature ranging from about 80° C. to about 250° C.

18. The process as defined by claim 15, wherein the molar ratio of sequestering agent (III) to the alkali metal hydroxide ranges from about 0.001 to about 0.2.

19. The process as defined by claim 18, said molar ratio ranging from about 0.01 to about 0.1.

20. The process as defined by claim 10, wherein there is prepared ortho-, meta- or para-chloroanisole, 2,3-dichloroanisole, 2,6-dichloroanisole, 2,5-dichloroanisole, 2,4,5-trichloroanisole, 2,3,6-trichloroanisole, 2,3,4,6-tetrachloroanisole, pentachloroanisole, 2,3-dichloroethoxybenzene, 2,5-dichloroethoxybenzene, or 2,5-dichloroisopropoxybenzene.

* * * * *